(12) United States Patent
Liu (10) Patent No.: US 9,955,731 B2
(45) Date of Patent: May 1, 2018

(54) ATOMIZER AND ELECTRONIC CIGARETTE WITH CYLINDRICAL PRESSED-WIRE HEATING ELEMENT

(71) Applicant: KIMREE HI-TECH INC., RoadTown, Tortola (VG)

(72) Inventor: Qiuming Liu, Guangdong (CN)

(73) Assignee: HUIZHOU KIMREE TECHNOLOGY CO., LTD. SHENZHEN BRANCH, Shenzhen, Guangdong (CN)

( * ) Notice: Subject to any disclaimer, the term of this patent is extended or adjusted under 35 U.S.C. 154(b) by 392 days.

(21) Appl. No.: 14/712,172

(22) Filed: May 14, 2015

(65) Prior Publication Data
US 2015/0305408 A1   Oct. 29, 2015

Related U.S. Application Data

(63) Continuation of application No. PCT/CN2014/080187, filed on Jun. 18, 2014.

(30) Foreign Application Priority Data

Apr. 24, 2014   (CN) .................... 2014 2 0203993 U (51) Int. Cl.
A24F 13/00   (2006.01)
A24F 47/00   (2006.01)
(Continued)

(52) U.S. Cl.
CPC .............. *A24F 47/008* (2013.01); *A24F 1/04* (2013.01); *A24F 7/00* (2013.01); *H05B 3/06* (2013.01);
(Continued)

(58) Field of Classification Search
CPC ........ A24F 1/04; A24F 7/00; A61L 2209/135; B41J 2/14088; H05B 3/00
(Continued)

(56) References Cited

U.S. PATENT DOCUMENTS

| | | | |
|---|---|---|---|
| 2013/0192618 A1 | 8/2013 | Li et al. | |
| 2014/0060554 A1* | 3/2014 | Collett | H05B 3/265 131/328 |

(Continued)

FOREIGN PATENT DOCUMENTS

| | | |
|---|---|---|
| CN | 203121009 U | 8/2013 |
| CN | 203327956 U | 12/2013 |

(Continued)

OTHER PUBLICATIONS

International Search Report corresponding to Application No. PCT/JP2014/080187; dated Feb. 24, 2014.

*Primary Examiner* — Abdullah Riyami
*Assistant Examiner* — Justin Kratt
(74) *Attorney, Agent, or Firm* — U.S. Fairsky LLP; Yue Xu (57) ABSTRACT

An atomizer and an electronic cigarette are provided by the present application. The atomizer includes an atomizing sleeve, a cigarette liquid storage space disposed in the atomizing sleeve, an electrical heating element, and a liquid guiding pipe. The electrical heating element is of a hollow cylindrical shape, and an axis of the cylindrical electrical heating element is in parallel with or coincides with an axis of the atomizer. The electrical heating element is wrapped by the liquid guiding pipe, thus, due to the liquid guiding pipe, the cigarette liquid can be uniformly delivered to the electrical heating element, and the amount of smoke atomized by the electrical heating element is uniform and constant, which improves the user experience. Further, the cylindrical shape effectively increases the length of the electrical heating (Continued)

element and the contact area between the electrical heating element and the cigarette liquid.

20 Claims, 6 Drawing Sheets (51) Int. Cl.
*A24F 1/04* (2006.01)
*A24F 7/00* (2006.01)
*H05B 3/06* (2006.01)
*H05B 3/44* (2006.01)
*H05B 3/00* (2006.01)
*B41J 2/14* (2006.01)

(52) U.S. Cl.
CPC .......... *H05B 3/44* (2013.01); *A61L 2209/135* (2013.01); *B41J 2/14088* (2013.01); *H05B 3/00* (2013.01); *H05B 2203/022* (2013.01)

(58) Field of Classification Search
USPC ........... 131/329, 328, 202; 29/611; 392/404, 392/397
See application file for complete search history.

(56) References Cited

U.S. PATENT DOCUMENTS

| 2015/0007835 | A1* | 1/2015 | Liu | ........................ | A24F 47/008 |
| | | | | | 131/329 |
| 2015/0101626 | A1* | 4/2015 | Li | ........................ | H01M 2/105 |
| | | | | | 131/329 |
| 2015/0164142 | A1* | 6/2015 | Li | ........................ | A24F 47/008 |
| | | | | | 131/329 |
| 2016/0021931 | A1* | 1/2016 | Hawes | .................. | A24F 47/008 |
| | | | | | 131/328 |

FOREIGN PATENT DOCUMENTS

| CN | 103519350 A | 1/2014 |
| CN | 203467675 U | 3/2014 |
| CN | 203523811 U | 4/2014 |

* cited by examiner

Figure 1

PRIOR ART

ATOMIZER AND ELECTRONIC CIGARETTE WITH CYLINDRICAL PRESSED-WIRE HEATING ELEMENT

This application is a continuation of International Application No. PCT/CN2014/080187, titled "ATOMIZER AND ELECTRONIC CIGARETTE", filed on Jun. 18, 2014, which claims the benefit of priority to Chinese Patent Application No. 201420203993.8 titled "ATOMIZER AND ELECTRONIC CIGARETTE", filed with the Chinese State Intellectual Property Office on Apr. 24, 2014, both of which applications are incorporated herein in their entireties by this reference.

TECHNICAL FIELD

The present application relates to the technical field of electronic cigarettes, and particularly to an atomizer and an electronic cigarette which can effectively increase the amount of smoke.

BACKGROUND

Figure 1:
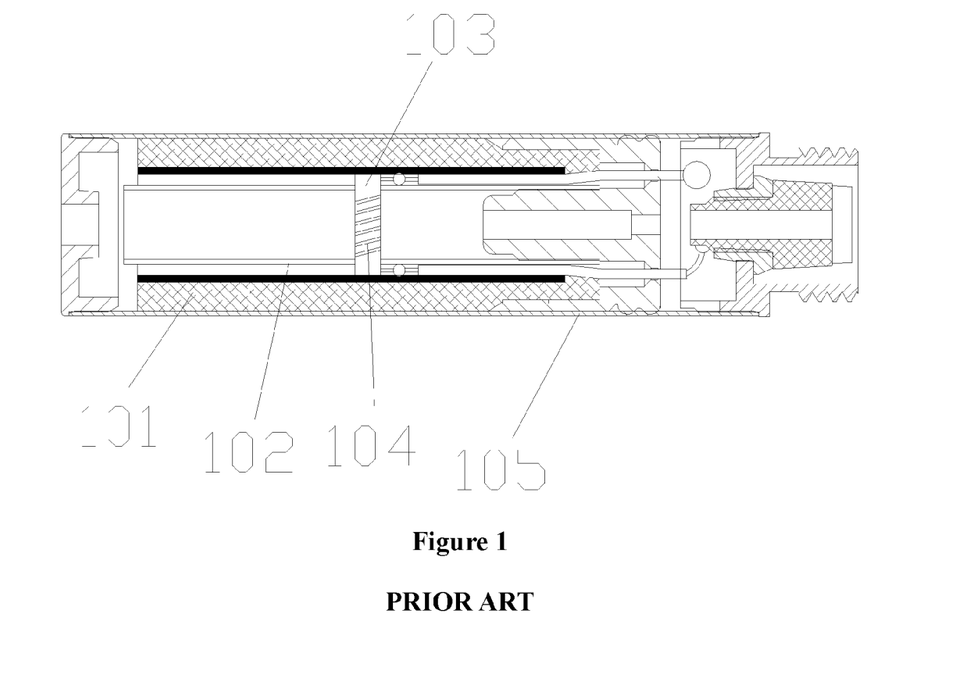
FIG. 1 is a sectional schematic view showing the structure of a conventional atomizer.

The structure of a conventional atomizer is shown in FIG. 1. As shown in FIG. 1, the atomizer is configured to atomize the cigarette liquid to form smoke that can be inhaled by a user. In a specific arrangement, a liquid guiding pipe 102 is arranged in an atomizing sleeve 105, and the liquid guiding pipe 102 is wrapped by a liquid storage cotton 101 configured to store the cigarette liquid. A glass fiber wire 103 is arranged in the liquid guiding pipe 102, and two ends of the glass fiber wire 103 pass through the liquid guiding pipe 102 and extend into the liquid storage cotton 101. A heating wire 104 for atomizing the cigarette liquid is wound around the glass fiber wire 103, and the axis of the heating wire 104 is perpendicular to the axis of the atomizer. The cigarette liquid stored in the liquid storage cotton 101 is delivered to the heating wire 104 by the liquid guiding pipe 102 and the glass fiber wire 103, to be atomized by the heating wire 104 to form smoke.

Currently, the diameter of the heating wire 104 ranges from 0.08 mm to 0.13 mm, which is relatively small, thus the contact area between the heating wire 104 and the glass fiber wire 103 is small. The temperature for atomizing the cigarette liquid ranges from 220° C. to 300° C. In order to increase the amount of smoke to satisfy the requirement of a user having a great vital capacity, the current passing through the heating wire 104 is increased to enable the temperature of the heating wire 104 to reach 300° C. to 600° C. after being powered. However, this manner is apt to burn the liquid storage cotton 101, which affects the service life of the electronic cigarette. In addition, another manner for increasing the amount of smoke is realized by increasing the length of the heating wire 104; however, since the electronic cigarette needs to imitate a real cigarette, the electronic cigarette is preferable to have a shape identical to the real cigarette to be more easily accepted by the user. Thus, the electronic cigarette and the liquid guiding pipe 102 in the electronic cigarette both have a limited sectional area, and the increase in the length of the heating wire 104 is limited, thus the increase in the amount of smoke atomized by the heating wire 104 is also limited. Further, if the heating wire 104 is too long, the cigarette liquid cannot be delivered to the middle of the heating wire 104, and can only be atomized at two ends of the heating wire 104, thus, the middle of the heating wire 104 is apt to be burned.

SUMMARY

In view of this, an atomizer and an electronic cigarette are provided according to the present application, which can effectively increase the amount of smoke.

An atomizer includes an atomizing sleeve, a cigarette liquid storage space configured to store a cigarette liquid and arranged in the atomizing sleeve, an electrical heating element configured to atomize the cigarette liquid to form smoke, and a liquid guiding pipe configured to deliver the cigarette liquid to the electrical heating element to be atomized;

wherein, the electrical heating element is of a hollow cylindrical shape, and the electrical heating element is made by winding a heating wire which is pressed into a sheet structure, and an axis of the cylindrical electrical heating element is in parallel with or coincides with an axis of the atomizer; and the liquid guiding pipe is arranged inside the cigarette liquid storage space, and the electrical heating element is wrapped by the liquid guiding pipe.

In the atomizer, the electrical heating element is made by winding the heating wire, which is pressed into the sheet structure, in a radial direction of the atomizing sleeve to form a cylindrical spiral spring shape;

or, the electrical heating element is made by winding a plurality of heating wires, which are each pressed into the sheet structure, in parallel in a radial direction of the atomizing sleeve to form a cylindrical spiral spring shape.

In the atomizer, the electrical heating element is made by repeatedly bending the heating wire, which is pressed into the sheet structure, in an axial direction of the atomizing sleeve and laying the bent heating wire in the liquid guiding pipe to form a cylindrical shape, or, the electrical heating element is made by repeatedly bending a plurality of heating wires, which are in parallel to each other, in an axial direction of the atomizing sleeve and laying the bent heating wires in the liquid guiding pipe to form a cylindrical shape.

In the atomizer, the electrical heating element includes a first sheet-like arc-shaped body and a second sheet-like arc-shaped body which are connected, the first sheet-like arc-shaped body and the second sheet-like arc-shaped body are cooperatively arranged in the liquid guiding pipe to form a cylindrical shape; and the first sheet-like arc-shaped body and the second sheet-like arc-shaped body are each made by repeatedly bending the heating wire, which is pressed into the sheet structure, in an axial direction or a radial direction of the atomizing sleeve and laying the bent heating wire in the liquid guiding pipe.

In the atomizer, the cigarette liquid storage space includes:

a first liquid storage cotton accommodated in the atomizing sleeve and configured to store the cigarette liquid, wherein the liquid guiding pipe is wrapped by the first liquid storage cotton;

or, the cigarette liquid storage space includes:

a liquid storage cavity provided inside the atomizing sleeve and configured to store the cigarette liquid;

a liquid partitioning pipe inserted in the liquid storage cavity and configured to prevent the cigarette liquid from being overly delivered to the liquid guiding pipe, wherein a through hole for delivering the cigarette liquid is provided on the liquid partitioning pipe; and a second liquid storage cotton accommodated in the liquid partitioning pipe;

wherein the liquid guiding pipe is wrapped by the second liquid storage cotton.

The atomizer further includes:

a first outer electrode inserted in the atomizing sleeve;

an insulating ring mounted in the first outer electrode; and a first inner electrode inserted in the insulating ring;

wherein the electrical heating element has one end inserted between the first outer electrode and the atomizing sleeve, and another end inserted between the first inner electrode and the insulating ring.

In the atomizer, the atomizing sleeve is a member made of a non-metallic material, and an annular protrusion is provided on a circumferential surface on an inner wall of the atomizing sleeve, and a retaining groove configured to cooperate with the protrusion is provided on an outer circumferential wall of the first outer electrode at a position corresponding to the protrusion.

An electronic cigarette includes an electronic cigarette body;

the electronic cigarette body is provided with a suction end, the atomizer according to any one of the above solutions, and a battery rod assembly for powering the atomizer;

the battery rod assembly is arranged at an end of the electronic cigarette body away from the suction end, or, the atomizer is arranged at an end of the electronic cigarette body away from the suction end.

In the electronic cigarette, the battery rod assembly includes:

a battery sleeve;

a battery disposed in the battery sleeve;

a second outer electrode and a second inner electrode electrically connected to the battery, respectively, the second outer electrode being electrically connected to the first outer electrode, and the second inner electrode being electrically connected to the first inner electrode;

a sensing module configured to generate a trigger signal according to an operation of a user; and a microcontroller electrically connected to the sensing module and configured to generate a control signal according to the trigger signal, wherein the microcontroller is configured to control, via the control signal, the battery to supply power to the electrical heating element.

In the electronic cigarette, the atomizer is coaxially arranged with the battery rod assembly, and the atomizer is detachably connected to the battery rod assembly.

In the electronic cigarette, the suction end is formed by an extension of an end of the atomizer away from the battery rod assembly, or, the suction end is detachably connected to an end of the atomizer away from the battery rod assembly.

In the electronic cigarette, the suction end is formed by an extension of an end of the battery rod assembly away from the atomizer or, the suction end is detachably connected to an end of the battery rod assembly away from the atomizer.

In the electronic cigarette, the liquid guiding pipe is a glass fiber pipe made of glass fiber.

An atomizer and an electronic cigarette are provided by the present application. The atomizer includes an atomizing sleeve, a cigarette liquid storage space disposed in the atomizing sleeve, an electrical heating element, and a liquid guiding pipe. The electrical heating element is of a hollow cylindrical shape, and an axis of the cylindrical electrical heating element is in parallel with or coincides with an axis of the atomizer. In the present application, the electrical heating element is wrapped by the liquid guiding pipe, thus, due to the liquid guiding pipe, the cigarette liquid can be uniformly delivered to the electrical heating element, and the amount of smoke atomized by the electrical heating element is uniform and constant, which improves the user experience. Further, the cylindrical shape effectively increases the length of the electrical heating element and the contact area between the electrical heating element and the cigarette liquid, thereby avoiding the problem in the conventional technology that the requirements of the user on the amount of smoke cannot be satisfied due to the limited contact area between the heating wire and the cigarette liquid. Thus the atomizer according the present application may greatly increase the amount of smoke without burning parts such as the cigarette liquid storage cotton, and the service life and usage safety of the atomizer is ensured and the qualified rate of the product is increased.

BRIEF DESCRIPTION OF THE DRAWINGS

For more clearly illustrating embodiments of the present application or the technical solution in the conventional technology, drawings referred to describe the embodiments or the conventional technology will be briefly described hereinafter. Apparently, the drawings in the following description are only several embodiments of the present application, and for the person skilled in the art, other drawings may be obtained based on these drawings without any creative efforts.

DETAILED DESCRIPTION

A first embodiment is provided according to the present application, which describes the specific structure of an atomizer in detail. The structure of the atomizer is shown in FIG. 2 and FIG. 3.

Figure 2:
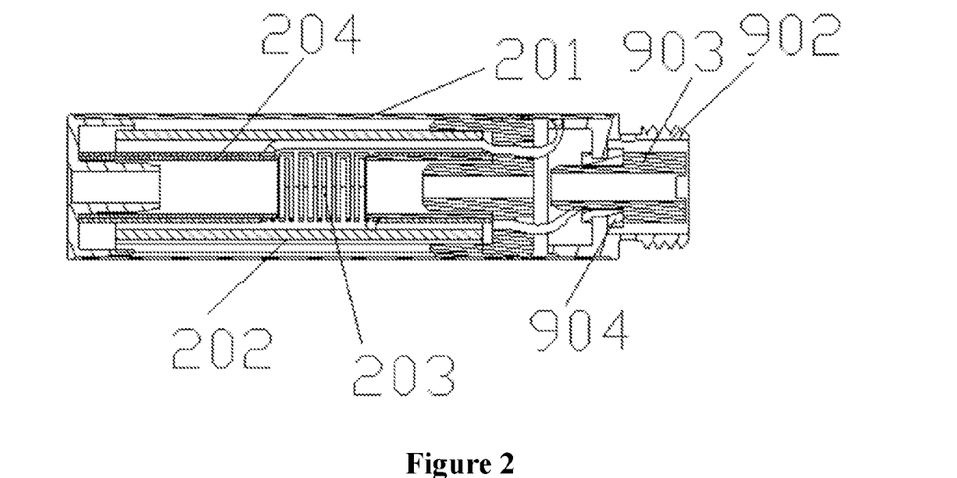
FIG. 2 is a sectional schematic view showing the structure of a preferred embodiment of an atomizer according to the present application.
Figure 3:
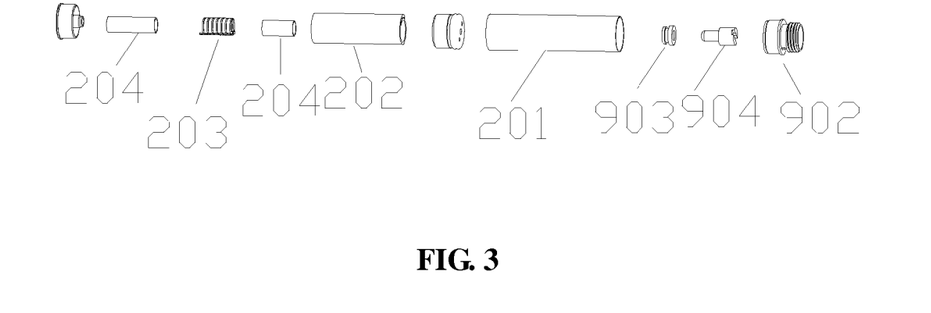
FIG. 3 is an exploded schematic view showing the structure of the preferred embodiment of the atomizer according to the present application.

FIG. 2 is a sectional schematic view showing the structure of a preferred embodiment of an atomizer according to the present application; and FIG. 3 is an exploded schematic view showing the structure of the preferred embodiment of the atomizer according to the present application.

The atomizer includes an atomizing sleeve 201. A cigarette liquid storage space 202 for storing a cigarette liquid is arranged in the atomizing sleeve 201. The cigarette liquid may be hermetically stored in the cigarette liquid storage space 202.

The atomizer further includes an electrical heating element 203 for atomizing the cigarette liquid to form smoke.

The cigarette liquid may be atomized by the electrical heating element 203 to form smoke that can be inhaled by a user.

The electrical heating element 203 is of a hollow cylindrical shape, which can be referred to FIG. 3.

The electrical heating element 203 may be formed by winding a heating wire which is pressed into a sheet structure. The axis of the cylindrical electrical heating element 203 may be parallel to or coincide with the axis of the atomizer.

In this embodiment, the axis of the electrical heating element 203 is configured to coincide with the axis of the atomizer, to improve the qualified rate of the product, facilitate assembling, and increase the amount of smoke atomized by the electrical heating element 203 as much as possible.

The electrical heating element 203 in this embodiment may atomize the cigarette liquid to form smoke, and the smoke can be discharged through the hollow of the electrical heating element 203.

The atomizer further includes a liquid guiding pipe 204 for delivering the cigarette liquid to the electrical heating element 203 to be atomized.

The liquid guiding pipe 204 is arranged in the cigarette liquid storage space 202, and the electrical heating element 203 is wrapped by the liquid guiding pipe 204.

Since the electrical heating element 203 is wrapped by the liquid guiding pipe 204 in this embodiment, the contact area between the electrical heating element 203 and the cigarette liquid storage space 202 is larger than that in the conventional technology, thereby increasing the amount of smoke effectively. Further, the outer circumferential surface of the electrical heating element 203 is in contact with the cigarette liquid storage space 202 uniformly, which avoids a situation in the conventional technology that the heating wire not in contact with the liquid storage cotton is burnt.

Further, the electrical heating element 203 with a large area may be arranged in the liquid guiding pipe 204 with a small dimension, thereby increasing the amount of smoke atomized by the electrical heating element 203, allowing the user to smoke enough smoke and ensuring the user experience.

The liquid guiding pipe 204 may be a glass fiber pipe made of glass fiber material, which has a property of absorbing the cigarette liquid and a good heat resistance, thus it can better avoid the burning situation. The liquid guiding pipe 204 can deliver the cigarette liquid stored in the cigarette liquid storage space 202 to the electrical heating element 203 uniformly and constantly, thereby effectively preventing the backflow of the cigarette liquid and avoiding the leakage of the cigarette liquid.

Further, the electrical heating element 203 is wrapped by the liquid guiding pipe 204, thus if the electrical heating element 203 has a high temperature during atomizing the cigarette liquid, the liquid guiding pipe 204 may dissipate the heat of the electrical heating element 203 uniformly, which avoids the electrical heating element 203 having the high temperature from burning the members inside the cigarette liquid storage space 202. Therefore, when using the atomizer according to the present application, the user does not need to worry about that the members inside the cigarette liquid storage space 202 may be burned which causes the atomizer to be unable to operate normally, even if the atomizer is used for a long time.

A second embodiment is provided according to the present application, and the specific structure of the electrical heating element 203 is described in detail in this embodiment.

The electrical heating element 203 may have the following arrangements.

Figure 4:
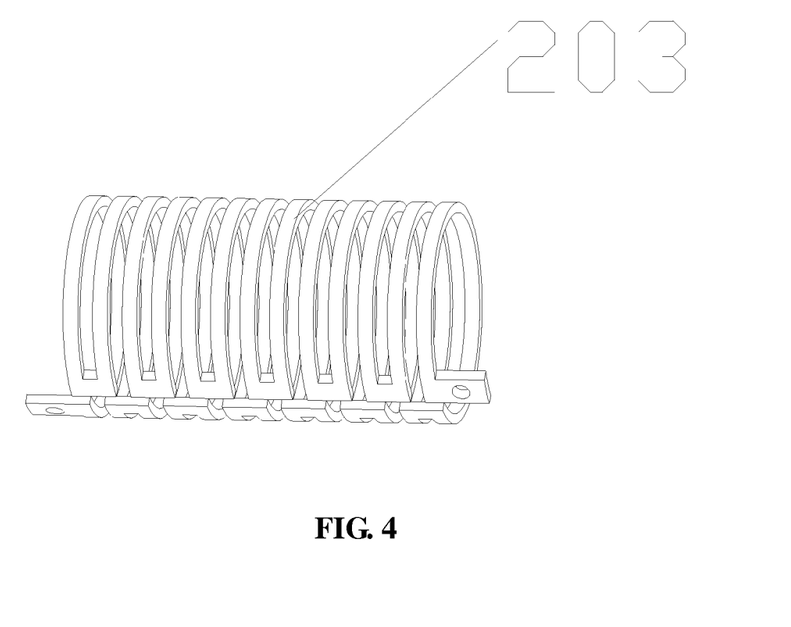
FIG. 4 is a schematic view showing the overall structure of a preferred embodiment of an electrical heating element of the atomizer according to the present application.
Figure 5:
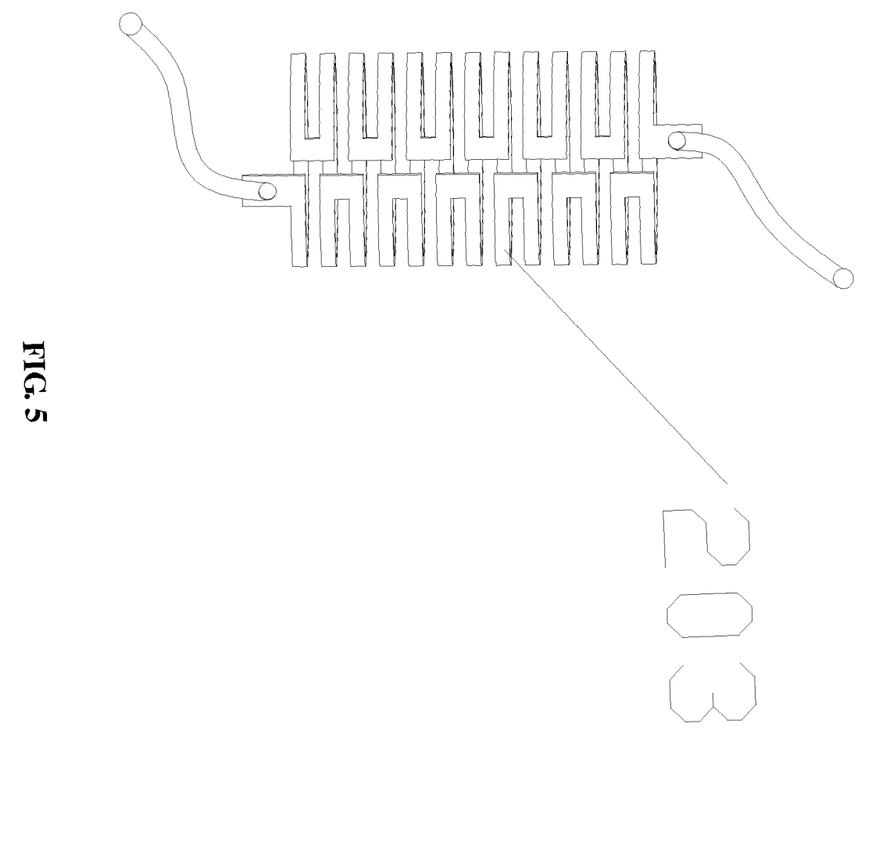
FIG. 5 is a sectional schematic view showing the structure of the preferred embodiment of the electrical heating element of the atomizer according to the present application.

A first arrangement is shown in FIG. 4 and FIG. 5.

A heating wire, which is pressed into a sheet structure, is wound in the radial direction of the atomizing sleeve 201 to form a cylindrical spiral spring shape, thereby forming the electrical heating element 203.

As shown in FIG. 4 and FIG. 5, the electrical heating element 203 is formed by pressing the heating wire of the sheet structure. Thus, the electrical heating element 203 has a stable and reliable structure, and various circles of the spiral of the electrical heating element 203 will not contact each other even under the effect of the gravity or a shock. Therefore, the circles of the spiral of the electrical heating element 203 can still atomize the cigarette liquid uniformly, thereby improving the user experience and the qualified rate of the product.

In a second arrangement, a plurality of heating wires, being pressed into a sheet structure, are wound in the radial direction of the atomizing sleeve 201 in parallel to form a cylindrical spiral spring shape, thereby forming the electrical heating element 203.

Compared to the first arrangement, the second arrangement further increases the contact area between the electrical heating element 203 and the liquid guiding pipe 204, thereby further ensuring the amount of smoke.

Figure 6:
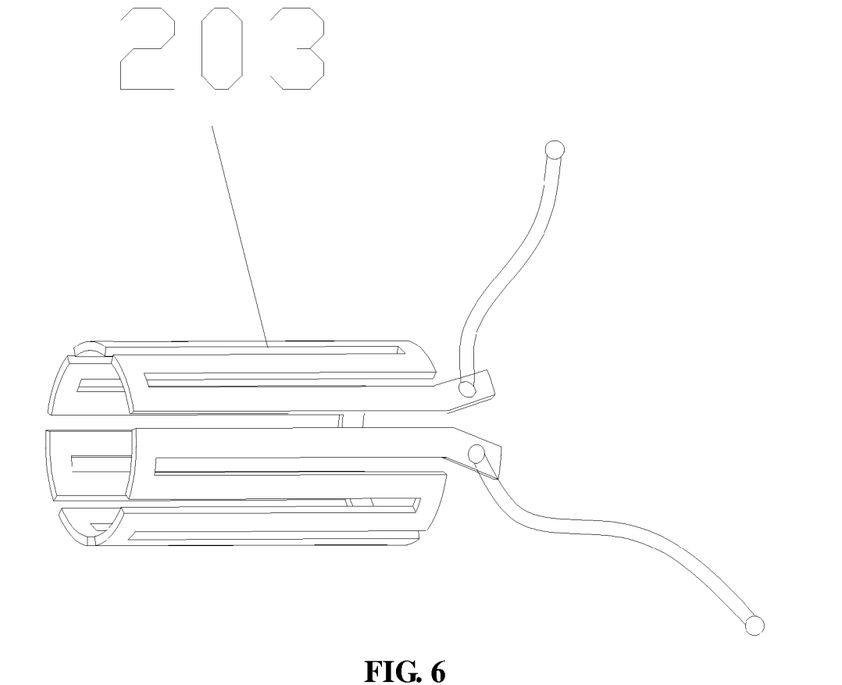
FIG. 6 is a schematic view showing the overall structure of another preferred embodiment of the electrical heating element of the atomizer according to the present application.

A third arrangement is shown in FIG. 6.

A heating wire, being pressed into a sheet structure, is bended in the axial direction of the atomizing sleeve 201 repeatedly and laid inside the liquid guiding pipe 204 to form a cylindrical shape, thereby forming the electrical heating element 203.

As shown in FIG. 6, the electrical heating element 203 is formed by pressing the heating wire of the sheet structure, thus, the electrical heating element 203 has a stable and reliable structure.

Figure 7:
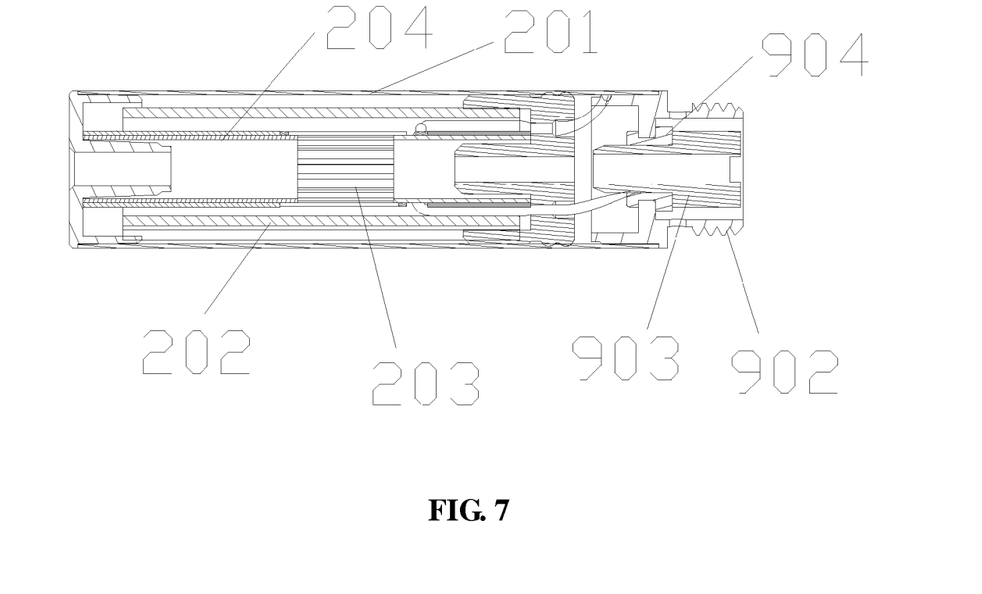
FIG. 7 is a sectional schematic view showing the structure of another preferred embodiment of the atomizer according to the present application.

The specific structure of the atomizer provided with the electrical heating element 203 according to this arrangement is shown in FIG. 7.

As shown in FIG. 7, the electrical heating element 203 is formed by repeatedly bending the heating wire in the axial direction of the atomizing sleeve 201, thus adjacent heating wires of the electrical heating element 203 will not contact each other even under the effect of the gravity or a shock. Therefore, the heating wires of the electrical heating element 203 can still atomize the cigarette liquid uniformly, thereby improving the user experience and the qualified rate of the product.

In a fourth arrangement, a plurality of parallel heating wires are bended in the axial direction of the atomizing sleeve 201 repeatedly and laid inside the liquid guiding pipe 204 to form a cylindrical shape, thereby forming the electrical heating element 203.

Compared to the third arrangement, the fourth arrangement further increases the contact area between the electrical heating element 203 and the liquid guiding pipe 204, thereby further ensuring the amount of smoke.

Further, an electronic wire may be provided at both ends of the electrical heating element 203 by welding, thus the electrical heating element 203 is electrically connected to electrodes of the atomizer via the electronic wires.

Figure 8:
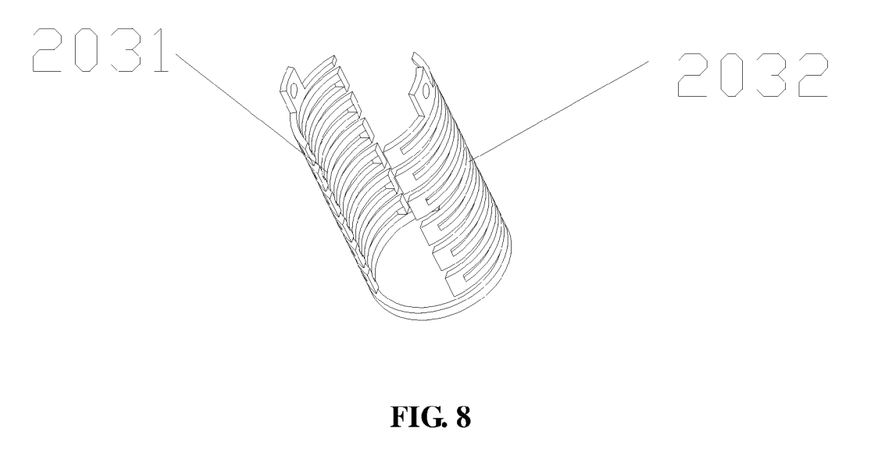
FIG. 8 is a schematic view showing the overall structure of another preferred embodiment of the electrical heating element of the atomizer according to the present application.

A fifth arrangement is shown in FIG. 8.

The electrical heating element 203 includes a first sheet-like arc-shaped body 2031 and a second sheet-like arc-shaped body 2032 which are connected to each other.

The first sheet-like arc-shaped body 2031 and the second sheet-like arc-shaped body 2032 are cooperatively arranged inside the liquid guiding pipe 204 to form a cylindrical shape.

The first sheet-like arc-shaped body 2031 and the second sheet-like arc-shaped body 2032 are each made by pressing the sheet-like heating wire. Thus, the first sheet-like arc-shaped body 2031 and the second sheet-like arc-shaped body 2032 each have a stable and reliable structure, and various circles of the spiral of the electrical heating element 203 will not contact each other even under the effect of the gravity or a shock. Therefore, the circles of the spiral of the electrical heating element 203 can still atomize the cigarette liquid uniformly, thereby improving the user experience and the qualified rate of the product.

The first sheet-like arc-shaped body 2031 and the second sheet-like arc-shaped body 2032 shown in FIG. 8 are each formed by repeatedly bending the heating wire, being pressed into a sheet structure, in the radial direction of the atomizing sleeve 201 and then laying the heating wire inside the liquid guiding pipe.

Certainly, each of the first sheet-like arc-shaped body 2031 and the second sheet-like arc-shaped body 2032 may also be formed by repeatedly bending the heating wire, being pressed into a sheet structure, in the axial direction of the atomizing sleeve 201 and then laying the heating wire inside the liquid guiding pipe The specific arrangement in this embodiment will not be described in detail.

Figure 9:
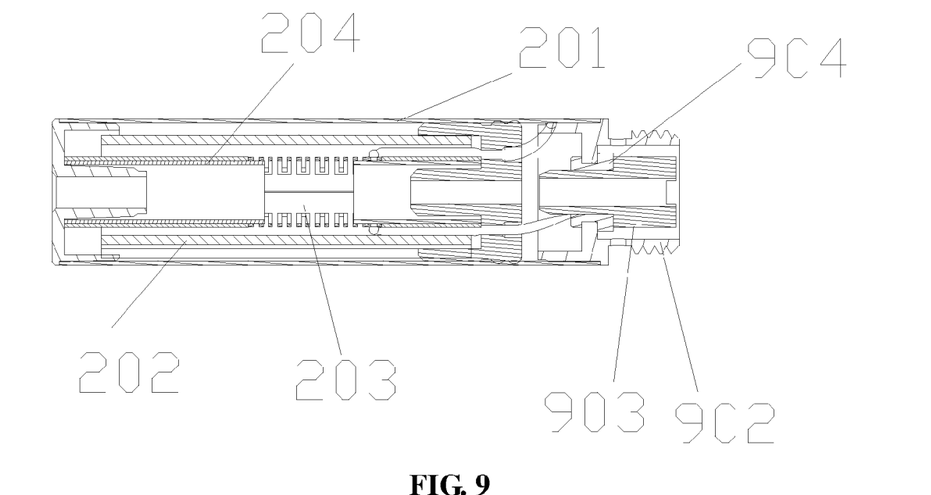
FIG. 9 is a sectional schematic view showing the structure of another preferred embodiment of the atomizer according to the present application.

The specific structure of the atomizer having the electrical heating element 203 shown in FIG. 8 is shown in FIG. 9.

A third embodiment is provided according to the present application, and the specific structure of the cigarette liquid storage space of the atomizer is described in detail in this embodiment.

In a first arrangement, the cigarette liquid storage space 202 is a first liquid storage cotton configured to store the cigarette liquid and accommodated inside the atomizing sleeve 201. The liquid guiding pipe 204 is wrapped by the first liquid storage cotton. Since the liquid guiding pipe 204 is wrapped by the first liquid storage cotton, the liquid guiding pipe 204 can deliver the cigarette liquid stored in the first liquid storage cotton to the electrical heating element 203 uniformly and constantly, thereby making the smoke atomized by the electrical heating element 203 uniform and constant, and ensuring the taste of the smoke inhaled by the user.

In a second arrangement, the cigarette liquid storage space 202 includes a liquid storage cavity disposed in the atomizing sleeve to store the cigarette liquid, wherein the cigarette liquid in a liquid state is stored in the liquid storage cavity.

The cigarette liquid storage space 202 includes a liquid partitioning pipe inserted in the liquid storage cavity and configured to prevent the cigarette liquid from being overly delivered to the liquid guiding pipe, wherein the liquid partitioning pipe is provided with a through hole for delivering the cigarette liquid. A second liquid storage cotton is arranged inside the liquid partitioning pipe, thus the cigarette liquid stored in the liquid storage cavity may be delivered to the second liquid storage cotton uniformly and constantly via the through hole on the liquid partitioning pipe, which prevents the cigarette liquid in the liquid storage cavity from being overly delivered to the second liquid storage cotton, and effectively prevents the leakage of the cigarette liquid.

The liquid guiding pipe is wrapped by the second liquid storage cotton, thus the second liquid storage cotton may deliver the cigarette liquid to the electrical heating element 203 uniformly.

In a third arrangement, the cigarette liquid storage space 202 includes a liquid storage cavity disposed in the atomizing sleeve to store the cigarette liquid, wherein the cigarette liquid in a liquid state is stored in the liquid storage cavity.

The liquid guiding pipe is directly inserted in the liquid storage cavity to increase the storage capacity of the atomizer for the cigarette liquid.

It is to be noted that, the above description for the structure of the cigarette liquid storage space 202 is only an example, and is not intended to limit this embodiment, and the structure of the cigarette liquid storage space 202 is not limited, as long as the cigarette liquid storage space 202 is capable of delivering the cigarette liquid to the electrical heating element 203 uniformly.

A fourth embodiment is provided according to the present application, and the specific structure of the atomizer is further described in this embodiment.

The specific structure of the atomizer is shown in FIG. 2, FIG. 3, FIG. 7, or FIG. 9.

The atomizer further includes a first outer electrode 902 inserted in the atomizing sleeve 201, an insulating ring 903 mounted in the first outer electrode 902, and a first inner electrode 904 inserted in the insulating ring 903.

Preferably, the first outer electrode 902 is provided with a threaded section, and the atomizer may be detachably connected to a battery rod assembly for powering the atomizer via the first outer electrode 902 with the threaded section.

That is, the insulating ring 903 is arranged between the first outer electrode 902 and the first inner electrode 904.

Referring to FIG. 2, FIG. 7, or FIG. 9, in this embodiment, in order to simplify the assembly process and improve the assembly efficiency, one end of the electrical heating element 203 is inserted between the first outer electrode 902 and the atomizing sleeve 201, and another end of the electrical heating element 203 is inserted between the first inner electrode 904 and the insulating ring 903.

That is, the electrical heating element 203 is fixed in the atomizer by inserting one end between the first outer electrode 902 and the atomizing sleeve 201 and inserting the other end between the first inner electrode 904 and the insulating ring 903.

Certainly, two ends of the electrical heating element 203 may each be provided with an electronic wire by welding, and the two electronic wires electrically connected to the electrical heating element 203 are, respectively, inserted between the first outer electrode 902 and the atomizing sleeve 201 and between the first inner electrode 904 and the insulating ring 903.

It is to be noted that, the above arrangement is only a preferred example, is not intended to limit the present application. In order to simplify the assembly process, one end of the electrical heating element 203 may also be inserted between the first outer electrode 902 and the insulating ring 903, and the other end of the electrical heating element 203 may be inserted between the first inner electrode 904 and the insulating ring 903. The specific arrangement is not limited in this embodiment, as long as the first inner electrode 904 is electrically connected to the atomizing electrode assembly by insertion, not by welding.

In this embodiment, the electrical heating element 203 is electrically connected to the atomizing electrode assembly by insertion, not by welding as in the conventional technology. Thus, in the specific assembly process, the assembly of the atomizer can be completed just by inserting one end of the electrical heating element 203 between the first outer electrode 902 and the atomizing sleeve 201 and inserting the other end of the electrical heating element 203 between the first inner electrode 904 and the insulating ring 903, without complicated operations. Therefore, the assembly is simple, which improves the assembly efficiency, saves the production cost, and lowers the requirement for the assemblers.

Further, in order to make the atomizer provided by this embodiment have an excellent sealing performance and prevent the leakage of the cigarette liquid in the cigarette liquid storage space 202, an annular protrusion is provided on a circumferential surface on the inner wall of the atomizing sleeve 201 made of a non-metallic material. A retaining groove configured to cooperate with the protrusion is provided on the outer circumferential surface of the first outer electrode 902 at a position corresponding to the protrusion.

Certainly, in order to allow the atomizer to have an excellent sealing performance, a first threaded section may be provided on the circumferential surface on the inner wall of the atomizing sleeve 201, and a second threaded section may be provided on the outer circumferential surface of the first outer electrode 902 at a position corresponding to the first threaded section. The atomizing sleeve 201 is threadedly coupled with the first outer electrode 902 by the threaded connection between the first threaded section and the second threaded section, thereby preventing the leakage of the cigarette liquid in the cigarette liquid storage space, and ensuring the excellent sealing performance of the atomizer.

Figure 10:
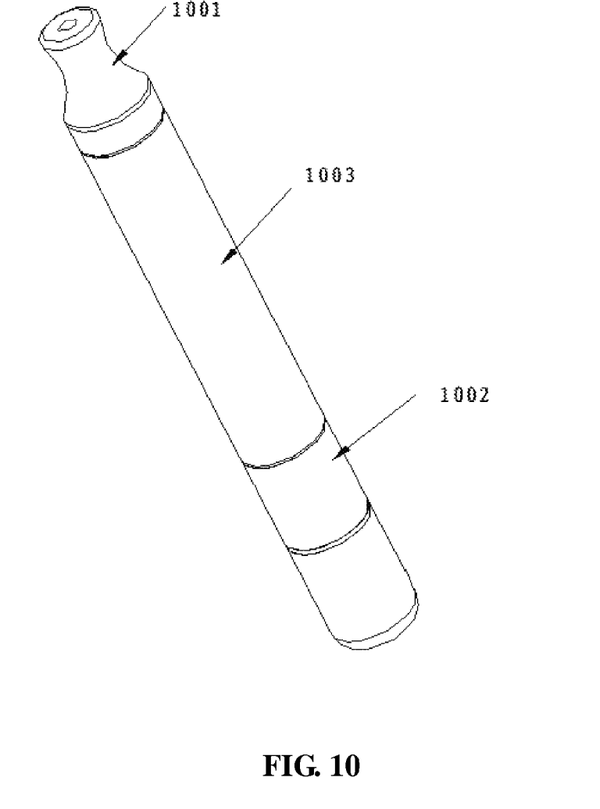
FIG. 10 is a schematic view showing the overall structure of a preferred embodiment of an electronic cigarette according to the present application.

An electronic cigarette using the above embodiments is provided according to a fifth embodiment. Referring to FIG. 10, the electronic cigarette includes an electronic cigarette body. The electronic cigarette body is provided with a suction end 1001, an atomizer 1002 described in the above embodiments, and a battery rod assembly for powering the atomizer 1002.

As shown in FIG. 10, the atomizer 1002 is arranged at an end of the electronic cigarette body away from the suction end 1001.

The above arrangement may have the following advantages. The atomizer 1002 is arranged away from the suction end 1001, thus a smoke channel for circulating the smoke in the electronic cigarette body does not pass through the atomizer 1002, which prevents the cigarette liquid which has not been atomized by the atomizer 1002 from leaking into the smoke channel. Therefore, the cigarette liquid which has not been atomized will not be inhaled by the user, thereby effectively avoiding the leakage of the cigarette liquid. Further, the smoke channel which does not pass through the atomizer 1002 may avoid the smoke from being condensed in the smoke channel, thereby effectively preventing the condensed cigarette liquid from blocking the smoke channel.

Further, the atomizer 1002 is arranged away from the suction end 1001, thus when a user smokes the electronic cigarette according to this embodiment, the heat generated by the atomizer 1002 in atomizing the cigarette liquid will not scald the user since the atomizer 1002 is away from the mouth of the user, thereby effectively improving the safety of using the electronic cigarette. Further, the user may generally hold the battery rod assembly 1003 when smoking, thus it avoids the user holding the hot atomizer 1002 for smoking, and when the user smokes the electronic cigarette provided by this embodiment, the hand of the user will not be scalded. Thus, the electronic cigarette provided by this embodiment effectively imitates the temperature of a real cigarette and promotes the using experience for the user.

The above arrangement of the electronic cigarette body is a preferred arrangement, and the arrangement of the electronic cigarette body is not limited to the above arrangement, for example, the battery rod assembly may also be arranged at an end of the electronic cigarette body away from the suction end.

In a sixth embodiment, the specific structure of the electronic cigarette is further described.

As shown in FIG. 10, the atomizer 1002 is preferably coaxially arranged with the battery rod assembly 1003, and the atomizer 1002 is detachably connected to the battery rod assembly 1003. With this arrangement, the appearance of the electronic cigarette may imitate a real cigarette visually, and the whole smoke channel is straight, which can effectively reduce the liquid accumulation.

The suction end 1001 is formed by an extension of an end of the battery rod assembly 1003 away from the atomizer, or, the suction end 1001 is detachably connected to the end of the battery rod assembly 1003 away from the atomizer 1002.

Preferably, the suction end may have a shape matching the mouth of the user, which further facilitates the user inhaling the smoke, and improves the user experience.

More preferably, the suction end 1001 is detachably connected to the battery rod assembly 1003 or the atomizer 1002, thereby facilitating replacing or cleaning the suction end 1001.

Further, the electronic cigarette body as a whole may have an irregular shape, and the irregular shape may be any shape. The atomizer assembly and the battery rod assembly are not coaxially arranged, for example, the atomizer and the battery rod assembly may be arranged in parallel, to enable the entire structure of the electronic cigarette to form a T shape.

For facilitating replacing the atomizer 1002, the atomizer 1002 is to the battery rod assembly 1003. For example, the atomizer 1002 and the battery rod assembly 1003 may be detachably connected by snap fit or threaded connection.

Figure 11:
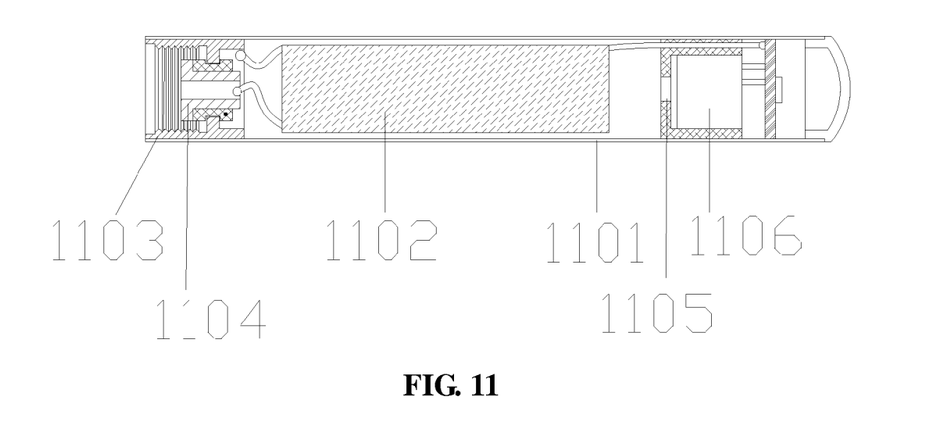
FIG. 11 is a sectional schematic view showing the structure of a preferred embodiment of a battery rod assembly of the electronic cigarette according to the present application.

A seventh embodiment is further provided according to the present application, and the specific structure of the battery rod assembly 1003 for cooperating with the atomizer shown in FIG. 2, FIG. 7, and FIG. 9 is described in conjunction with FIG. 11.

The battery rod assembly 1003 includes:

a battery sleeve 1101;

a battery 1102 disposed in the battery sleeve 1101;

a second outer electrode 1103 and a second inner electrode 1104 electrically connected to the battery 1102, respectively, the second outer electrode 1103 being electrically connected to the first outer electrode 902, and the second inner electrode 1104 being electrically connected to the first inner electrode 904; and a sensing module 1105 for generating a trigger signal according to an operation of a user.

In this embodiment, the sensing module 1105 is an air flow sensing switch for sensing the smoking action of the user to generate the trigger signal.

A microcontroller 1106 is electrically connected to the sensing module 1105 and is configured to generate a control signal according to the trigger signal, and the microcontroller 1106 controls, via the control signal, the battery 1102 to supply power to the electrical heating element 203.

The technical solutions in the embodiments of the present application will be described clearly and completely hereinafter in conjunction with the drawings in the embodiments of the present application. Apparently, the described embodiments are only a part of the embodiments of the present application, rather than all embodiments. Based on the embodiments in the present application, all of other embodiments, made by the person skilled in the art without any creative efforts, fall into the scope of the present application.

The above embodiments are described in a progressive manner. Each of the embodiments is mainly focused on describing its differences from other embodiments, and references may be made among these embodiments with respect to the same or similar portions among these embodiments.

Based on the above description of the disclosed embodiments, the person skilled in the art is capable of carrying out or using the present application. It is obvious for the person skilled in the art to make many modifications to these embodiments. The general principle defined herein may be applied to other embodiments without departing from the spirit or scope of the present application. Therefore, the present application is not limited to the embodiments illustrated herein, but should be defined by the broadest scope consistent with the principle and novel features disclosed herein.

The invention claimed is:

1. An atomizer, comprising an atomizing sleeve, a cigarette liquid storage space configured to store a cigarette liquid and arranged in the atomizing sleeve, an electrical heating element configured to atomize the cigarette liquid to form smoke, and a liquid guiding pipe configured to deliver the cigarette liquid to the electrical heating element to be atomized;

wherein, the electrical heating element is of a hollow cylindrical shape, and the electrical heating element is made by winding a heating wire which is pressed into a sheet structure, and an axis of the cylindrical electrical heating element is in parallel with or coincides with an axis of the atomizer; and the liquid guiding pipe is arranged inside the cigarette liquid storage space, and the liquid guiding pipe is divided into two parts along the axis of the atomizer and the electrical heating element is sandwiched between the two parts of the liquid guiding pipe.

2. The atomizer according to claim 1, wherein, the electrical heating element is made by winding the heating wire, which is pressed into the sheet structure, in a radial direction of the atomizing sleeve to form a cylindrical spiral spring shape;

or, the electrical heating element is made by winding a plurality of heating wires, which are each pressed into the sheet structure, in parallel in a radial direction of the atomizing sleeve to form a cylindrical spiral spring shape.

3. The atomizer according to claim 1, wherein, the electrical heating element is made by repeatedly bending the heating wire, which is pressed into the sheet structure, in an axial direction of the atomizing sleeve and laying the bent heating wire in the liquid guiding pipe to form a cylindrical shape;

or, the electrical heating element is made by repeatedly bending a plurality of heating wires, which are in parallel to each other, in an axial direction of the atomizing sleeve and laying the bent heating wires in the liquid guiding pipe to form a cylindrical shape.

4. The atomizer according to claim 1, wherein the electrical heating element comprises a first sheet-like arc-shaped body and a second sheet-like arc-shaped body which are connected, the first sheet-like arc-shaped body and the second sheet-like arc-shaped body are cooperatively arranged in the liquid guiding pipe to form a cylindrical shape; and the first sheet-like arc-shaped body and the second sheet-like arc-shaped body are each made by repeatedly bending the heating wire, which is pressed into the sheet structure, in an axial direction or a radial direction of the atomizing sleeve and laying the bent heating wire in the liquid guiding pipe.

5. The atomizer according to claim 1, wherein, the cigarette liquid storage space comprises a first liquid storage cotton accommodated in the atomizing sleeve and configured to store the cigarette liquid, wherein the liquid guiding pipe is wrapped by the first liquid storage cotton;

or, the cigarette liquid storage space comprises a liquid storage cavity provided inside the atomizing sleeve and configured to store the cigarette liquid, a liquid partitioning pipe inserted in the liquid storage cavity and configured to prevent the cigarette liquid from being overly delivered to the liquid guiding pipe, and a first liquid storage cotton accommodated in the liquid partitioning pipe; wherein a through hole for delivering the cigarette liquid is provided on the liquid partitioning pipe, and the liquid guiding pipe is wrapped by the first liquid storage cotton.

6. The atomizer according to claim 1, wherein the atomizer further comprises:

a first outer electrode inserted in the atomizing sleeve;

an insulating ring mounted in the first outer electrode; and a first inner electrode inserted in the insulating ring;

wherein a first electronic wire has one end attached to a first end of the electrical heating element and another end inserted between the first outer electrode and the atomizing sleeve, and a second electronic wire has one end attached to a second end of the electrical heating element and another end inserted between the first inner electrode and the insulating ring.

7. The atomizer according to claim 2, wherein the atomizer further comprises:
a first outer electrode inserted in the atomizing sleeve;
an insulating ring mounted in the first outer electrode; and
a first inner electrode inserted in the insulating ring;
wherein a first electronic wire has one end attached to a first end of the electrical heating element and another end inserted between the first outer electrode and the atomizing sleeve, and a second electronic wire has one end attached to a second end of the electrical heating element and another end inserted between the first inner electrode and the insulating ring.

8. The atomizer according to claim 3, wherein the atomizer further comprises:
a first outer electrode inserted in the atomizing sleeve;
an insulating ring mounted in the first outer electrode; and
a first inner electrode inserted in the insulating ring;
wherein a first electronic wire has one end attached to a first end of the electrical heating element and another end inserted between the first outer electrode and the atomizing sleeve, and a second electronic wire has one end attached to a second end of the electrical heating element and another end inserted between the first inner electrode and the insulating ring.

9. The atomizer according to claim 4, wherein the atomizer further comprises:
a first outer electrode inserted in the atomizing sleeve;
an insulating ring mounted in the first outer electrode; and
a first inner electrode inserted in the insulating ring;
wherein a first electronic wire has one end attached to a first end of the electrical heating element and another end inserted between the first outer electrode and the atomizing sleeve, and a second electronic wire has one end attached to a second end of the electrical heating element and another end inserted between the first inner electrode and the insulating ring.

10. The atomizer according to claim 5, wherein the atomizer further comprises:
a first outer electrode inserted in the atomizing sleeve;
an insulating ring mounted in the first outer electrode; and
a first inner electrode inserted in the insulating ring;
wherein a first electronic wire has one end attached to a first end of the electrical heating element and another end inserted between the first outer electrode and the atomizing sleeve, and a second electronic wire has one end attached to a second end of the electrical heating element and another end inserted between the first inner electrode and the insulating ring.

11. The atomizer according to claim 6, wherein the atomizing sleeve is a member made of a non-metallic material.

12. An electronic cigarette, comprising an electronic cigarette body;
wherein, the electronic cigarette body is provided with a suction end, an atomizer, and a battery rod assembly for powering the atomizer;
the atomizer comprises an atomizing sleeve, a cigarette liquid storage space configured to store a cigarette liquid and arranged in the atomizing sleeve, an electrical heating element configured to atomize the cigarette liquid to form smoke, and a liquid guiding pipe configured to deliver the cigarette liquid to the electrical heating element to be atomized;
wherein, the electrical heating element is of a hollow cylindrical shape, and the electrical heating element is made by winding a heating wire which is pressed into a sheet structure, and an axis of the cylindrical electrical heating element is in parallel with or coincides with an axis of the atomizer; and
the liquid guiding pipe is arranged inside the cigarette liquid storage space, and the liquid guiding pipe is divided into two parts along the axis of the atomizer and the electrical heating element is sandwiched between the two parts of the liquid guiding pipe; and
the battery rod assembly is arranged at an end of the electronic cigarette body away from the suction end, or, the atomizer is arranged at an end of the electronic cigarette body away from the suction end.

13. The electronic cigarette according to claim 12, wherein, the atomizer further comprises a first outer electrode inserted in the atomizing sleeve, an insulating ring mounted in the first outer electrode, and a first inner electrode inserted in the insulating ring; the battery rod assembly comprises:
a battery sleeve;
a battery disposed in the battery sleeve;
a second outer electrode and a second inner electrode electrically connected to the battery, respectively, the second outer electrode being electrically connected to the first outer electrode, and the second inner electrode being electrically connected to the first inner electrode;
a sensing module electrically connected to the battery and configured to generate a trigger signal according to an operation of a user; and
a microcontroller electrically connected to the sensing module and the battery and configured to generate a control signal according to the trigger signal, wherein the microcontroller is configured to control, via the control signal, the battery to supply power to the electrical heating element.

14. The electronic cigarette according to claim 12, wherein,
the atomizer is coaxially arranged with the battery rod assembly, and the atomizer is detachably connected to the battery rod assembly.

15. The electronic cigarette according to claim 12, wherein,
the suction end is formed by an extension of an end of the atomizer away from the battery rod assembly,
or,
the suction end is detachably connected to an end of the atomizer away from the battery rod assembly.

16. The electronic cigarette according to claim 12, wherein,
the suction end is formed by an extension of an end of the battery rod assembly away from the atomizer,
or,
the suction end is detachably connected to an end of the battery rod assembly away from the atomizer.

17. The electronic cigarette according to claim 12, wherein, the liquid guiding pipe is a glass fiber pipe made of glass fiber.

18. The electronic cigarette according to claim 12, wherein,
the electrical heating element is made by winding the heating wire, which is pressed into the sheet structure, in a radial direction of the atomizing sleeve to form a cylindrical spiral spring shape;
or,
the electrical heating element is made by winding a plurality of heating wires, which are each pressed into the sheet structure, in parallel in a radial direction of the atomizing sleeve to form a cylindrical spiral spring shape.

19. The electronic cigarette according to claim 12, wherein, the electrical heating element is made by repeatedly bending the heating wire, which is pressed into the sheet structure, in an axial direction of the atomizing sleeve and laying the bent heating wire in the liquid guiding pipe to form a cylindrical shape;

or, the electrical heating element is made by repeatedly bending a plurality of heating wires, which are in parallel to each other, in an axial direction of the atomizing sleeve and laying the bent heating wires in the liquid guiding pipe to form a cylindrical shape.

20. The electronic cigarette according to claim 12, wherein, the electrical heating element comprises a first sheet-like arc-shaped body and a second sheet-like arc-shaped body which are connected, the first sheet-like arc-shaped body and the second sheet-like arc-shaped body are cooperatively arranged in the liquid guiding pipe to form a cylindrical shape; and the first sheet-like arc-shaped body and the second sheet-like arc-shaped body are each made by repeatedly bending the heating wire, which is pressed into the sheet structure, in an axial direction or a radial direction of the atomizing sleeve and laying the bent heating wire in the liquid guiding pipe.

* * * * *